United States Patent [19]

Malik et al.

[11] Patent Number: 4,668,422

[45] Date of Patent: May 26, 1987

[54] LIQUID HAND-SOAP OR BUBBLE BATH COMPOSITION

[75] Inventors: Arshad H. Malik; Robert S. McDaniel, Jr.; Allen D. Urfer, all of Decatur, Ill.

[73] Assignee: A. E. Staley Manufacturing Company, Decatur, Ill.

[21] Appl. No.: 739,736

[22] Filed: May 31, 1985

[51] Int. Cl.$^4$ ................................................ C11D 3/22
[52] U.S. Cl. ............................. 252/174.17; 252/525; 252/528; 252/544; 252/547
[58] Field of Search ............ 252/174.17, 173, DIG. 5, 252/DIG. 13, DIG. 14, 117, 547, 528, 525, 544

[56] References Cited

U.S. PATENT DOCUMENTS

| | | | |
|---|---|---|---|
| 3,721,633 | 3/1973 | Ranauto | 252/527 |
| 4,284,534 | 8/1981 | Ehrlich | 252/DIG. 14 |
| 4,396,520 | 8/1983 | Payne et al. | 252/89.1 |
| 4,483,779 | 11/1984 | Llenado et al. | 252/135 |
| 4,483,780 | 11/1984 | Llenado | 252/174.17 |
| 4,483,787 | 11/1984 | Jones et al. | 252/551 |
| 4,493,773 | 1/1985 | Cook et al. | 252/8.8 |
| 4,555,360 | 11/1985 | Bissett et al. | 252/DIG. 14 |
| 4,606,850 | 8/1986 | Malik | 252/174.17 |

FOREIGN PATENT DOCUMENTS

| | | |
|---|---|---|
| 70074 | 1/1983 | European Pat. Off. . |
| 70075 | 1/1983 | European Pat. Off. . |
| 70076 | 1/1983 | European Pat. Off. . |
| 70077 | 1/1983 | European Pat. Off. . |
| 75994 | 4/1983 | European Pat. Off. . |
| 75995 | 4/1983 | European Pat. Off. . |
| 75996 | 4/1983 | European Pat. Off. . |
| 105556 | 4/1984 | European Pat. Off. . |
| 106692 | 4/1984 | European Pat. Off. . |

OTHER PUBLICATIONS

Physical and Functional Properties of Some Higher Alkyl Polyglycosides, Journal of the American Oil Chemists' Society, vol. 47, pp. 162-167, May 1970 by Hughes and Lew.

Liquid or Soft Soap, Household & Personal Product Industry, Oct. 1980, pp. 51-53, by Weistein and Smith.

Evaluation of Selected Liquid Hand-Soap Formulations, Cosmetic Technology Nov. 1981, pp. 33-42 by Kipers and Flynn.

*Primary Examiner*—Paul Lieberman
*Assistant Examiner*—Hoa Van Le
*Attorney, Agent, or Firm*—James B. Guffey; Michael F. Campbell; J. Daniel Wood

[57] ABSTRACT

Liquid hand-soap or bubble bath compositions are provided which comprise a glycoside surfactant, a nonionic foam booster and water and which have a viscosity of at least about 1,000 centipoise. Such compositions have a pleasing texture or consistency, are mild and fast rinsing and do not necessarily require the use of conventional moisturizing agents or additives. Preferred compositions further comprise an anionic or amphoteric surfactant material and especially preferred compositions contain an amphoteric surfactant and are substantially free of anionic surfactant components.

20 Claims, No Drawings

LIQUID HAND-SOAP OR BUBBLE BATH COMPOSITION

BACKGROUND OF THE INVENTION

The present invention pertains to liquid detergent compositions suitable for use as liquid hand-soap or bubble bath products. More particularly, such invention pertains to liquid hand-soap or bubble bath products or formulations which comprise a nonionic glycoside surfactant, a nonionic foam booster and water and which have a viscosity of at least about 1,000 cps.

Alkyl glycoside materials such as, for example, higher alkyl monoglycosides and higher alkyl polyglycosides are known materials; are known, at least in certain circumstances, to function as nonionic surfactants; and have been suggested as being suitable for use in certain specially formulated detergent compositions. See in this regard, for example, Published European Patent Application Nos. 0070074; 0070075; 0070076; and 0070077 (all of which published on Jan. 19, 1983) wherein certain alkylpolysaccharide surfactant/anionic surfactant mixtures have been suggested as being useful in such diverse end-use applications as laundry and personal cleaning products, diswashing, fire fighting, oil well drilling, ore benefication, solution mining, hair washing, formation of foamed solid structures etc. See also Published European Patent Application Nos. 0075994; 0075995; and 0075996 (all of which published on Apr. 6, 1983) wherein certain alkylpolysaccharide surfactant/nonionic surfactant mixtures are suggested for use in laundry detergent applications. Of the foregoing, Published European Application No. 0070076 appears to be particularly concerned with alkylpolysaccharide surfactant/anionic surfactant mixtures which further comprise an amide or amine oxide foam booster ingredient and Published Application No. 0075994 appears to be especially concerned with mixtures of alkylpolysaccharide surfactants with amine oxide surfactants and unsaturated fatty acid soaps. A variety of additional ingredients are generally suggested for possible or optional use within the foregoing Published European Applications including, for example, detergency builders, solvents, soil suspending agents, auxiliary surfactants such as zwitterionic and ampholytic or amphoteric surfactants, brighteners, fillers, perfumes, and the like.

Additional, recently published, patents or published patent applications pertaining to alkylpolyglycoside-containing detergent compositions include Published European Patent Application No. 0105556 (published Apr. 18, 1984) which discloses liquid detergent compositions containing anionic surfactants, selected nonionic surfactants and alkylpolyglycoside surfactants and which optionally can also contain a wide variety of other ingredients such as suds stabilizing amide or amine oxide surfactants, detergent builders, ampholytic, zwitterionic or cationic surfactants and the like; Published European Patent Application No. 0106692 (published Apr. 25, 1984) which discloses stable heavy-duty liquid detergent compositions containing a mixture of an ethoxylated fatty alcohol nonionic surfactant, an alkylpolyglycoside surfactant and a quaternary ammonium cationic surfactant in conjunction with a polyethylene glycol compound and a wide variety of optional conventional laundry detergent additives including, among many, many others, fatty amide surfactants, semi-polar nonionic surfactants such as trialkyl amine oxides, zwitterionic and ampholytic surfactants, detergent builders, bleaches, etc., etc.; U.S. Pat. No. 4,493,773 (issued Jan. 15, 1985) which discloses laundry detergent compositions which contain a conventional nonionic detergent surfactant, an alkylpolyglycoside detergent surfactant and a quaternary ammonium cationic fabric softening surfactant and which are said to be capable of including a wide variety of conventional laundry detergent additives such as relatively small amounts of detergent builders, detergency cosurfactants such as trialkyl amine oxide surfactants, zwitterionic surfactants, ampholytic surfactants, etc., solvents such as ethanol, and the like; U.S. Pat. No. 4,396,520 (issued Aug. 2, 1983) which discloses detergent compositions comprising mixtures of an alkylpolysaccharide surfactants and calcium sensitive anionic surfactants and which lists a multitude of potential optional ingredients such as builders, other detergent surfactants, brighteners, soil suspending agents, abrasives, dyes, fabric conditioning agents, hair conditioning agents, hydrotropes, solvents, fillers, etc.; and U.S. Pat. No. 4,483,787 (issued Nov. 20, 1984) which discloses concentrated aqueous detergent compositions comprising an alkyloligoglycoside surfactant and more than 35% of an alkylpolyethoxylate sulfate surfactant and which also includes a long listing of possible optional ingredients.

Higher alkyl polyglucosides and the use thereof as nonionic surfactants are also discussed in an article by Hughes and Lew entitled "Physical and Functional Properties of Some Higher Alkyl Polyglycosides", *Journal of the American Oil Chemists' Society*, Vol. 47, pages 162–167, May, 1970.

Aqueous built liquid detergents utilizing an alkyl glycoside surfactant in conjunction with a builder selected from the group consisting of potassium nitrilotriacetate, sodium nitrilotriacetate and a potassium polyphosphate are disclosed in U.S. Pat. No. 3,721,633 (issued Mar. 20, 1973).

Liquid or soft soap formulations are discussed in an article by Weistein and Smith entitled "Liquid or Soft Soap", *Household & Personal Products Industry*, Oct. 1980, pages 51–53 and in an article by Kipers and Flynn entitled "Evaluation of Selected liquid hand-soap formulations", *Cosmetic Technology*, November 1981, pages 33–42. Typically, such liquid hand-soap formulations have a solids content in the range of from 14 to 20 percent by weight; utilize an anionic surfactant as the main surfactant ingredient; and require the use of moisturizing ingredients.

The consumer market for soft or liquid hand-soap and bubble bath products is a growing and highly competitive one. As such, there is a continuing need or demand for new and improved and/or more economical liquid hand-soap and bubble bath products or formulations.

SUMMARY OF THE INVENTION

It has now been discovered that nonionic glycoside surfactants, when properly formulated with certain other ingredients as hereinafter discussed, are eminently well suited for use in liquid hand-soap and bubble bath compositions. Thus, there is provided in accordance with the present invention a liquid detergent composition which is suitable for use as a liquid hand-soap or bubble bath product and which comprises, on a total composition weight basis:

a. from about 3 to about 30 weight percent of a glycoside surfactant;

b. from about 1 to about 20 percent of a nonionic foam boosting surfactant, said foam boosting surfactant constituting about 50 weight percent or less of the total surfactant content of said composition; and c. up to about 95 weight percent water.

The compositions of the present invention are mild and fast rinsing and generally exhibit highly desirable foaming or lathering characteristics.

In a preferred embodiment, the compositions hereof further comprise, on a total composition weight basis, from about 2 to about 30 weight percent of an auxiliary surfactant selected from the group consisting of anionic surfactants, amphoteric surfactants, and mixtures thereof.

An especially preferred embodiment hereof is one in which an amphoteric surfactant is employed as the aforementioned auxiliary surfactant and wherein the resulting detergent composition is substantially free of anionic surfactant ingredients (e.g. which contains less than about 2, preferably less than about 1, weight percent of an anionic surfactant on a total composition weight basis). Unlike presently available commercial liquid hand-soaps which employ anionic surfactant materials and which typically require the use of moisturizing additives or ingredients, the compositions of this latter, especially preferred embodiment do not contain an anionic surfactant ingredient and do not require the use of moisturizing ingredients or additives.

The compositions hereof are also substantially different than previously suggested glycoside-containing liquid laundry detergent formulations which would typically have a viscosity of 300 centipoise or less (e.g., generally in the 200 to 300 centipoise range) and a solids content in excess of 30 weight percent and which would generally contain one or more commonly-used laundry detergent additives such as detergency builders, optical brighteners, antiredeposition agents, and the like. Unlike such liquid laundry detergent products, the hand-soap or bubble bath compositions hereof are characterized by having a viscosity of at least about 1000 centipoise and, most typically, a solids content of from about 10 to about 30 weight percent on a total weight basis and by being substantially free of the above-noted laundry detergent additives.

DETAILED DESCRIPTION OF THE INVENTION

Glycoside surfactants suitable for use in the practice of the present invention include those of the formula:

$$RO(R^1O)_y(Z)_x \quad\quad A$$

wherein R is a monovalent organic radical (e.g., a monovalent saturated aliphatic, unsaturated aliphatic or aromatic radical such as alkyl, hydroxylalkyl, alkenyl, hydroxyalkenyl, aryl, alkylaryl, hydroxyalkylaryl, arylalkyl, alkenylaryl, arylalkenyl, etc.) containing from about 6 to about 30 (preferably from about 8 to about 18 and more preferably from about 9 to about 13) carbon atoms; O is an oxygen atom; $R^1$ is a divalent hydrocarbon radical containing from 2 to about 4 carbon atoms such as ethylene, propylene or butylene (most preferably the unit $(R^1O)_y$ represents repeating units of ethylene oxide, propylene oxide and/or random or block combinations thereof); y is a number having an average value of from 0 to about 12; Z represents a moiety derived from a reducing saccharide containing 5 or 6 carbon atoms (most preferably a glucose unit); and x is a number having an average value of from 1 to about 10 (preferably from 1 to about 5, more preferably from 1 to about 3, and most preferably from about 1.2 to about 3).

Glycoside surfactants of the sort mentioned above, and various preferred subgenera thereof, are fully discussed in U.S. Pat. No. 4,483,779 to Llenado et al (issued Nov. 20, 1984) the discussion and description of which is hereby incorporated by reference.

Glycoside surfactants suitable for use herein also include those of the Formula A above in which one or more of the normally free (i.e., unreacted) hydroxyl groups of the saccharide moiety, Z, have been alkoxylated (preferably, ethoxylated or propoxylated) so as to attach one or more pendant alkoxy or poly (alkoxy) groups in place thereof. In such event, the amount of alkylene oxide (e.g., ethylene oxide, propylene oxide, etc.) employed will typically range from about 1 to about 20 (preferably from about 3 to about 10) moles thereof per mole of saccharide moiety within the Formula A glycoside material.

In glycosides of the Formula A above, the $RO(R^1O)_y$ group is generally bonded or attached to the number 1 carbon atom of the saccharide moiety, Z. Accordingly, the free hydroxyls available for alkoxylation are typically those in the number 2, 3, 4 and 6 positions in 6-carbon atom saccharides and those in the number 2, 3 and 4 positions in 5-carbon atom saccharide species. Typically, the number 2 position hydroxyls in 5-carbon saccharides, and the number 2 and 6 position hydroxyls in 6-carbon saccharides, are substantially more reactive or susceptible to alkoxylation than those in the number 3 and 4 positions. Accordingly, alkoxylation will usually occur in the former locations in preference to the latter. Examples of the indicated alkoxylated glycoside materials, and of methodology suitable for the preparations of same, are described in U.S. patent application Ser. No. 06/704,828 filed Feb. 22, 1985 by Roth et al.

Glycoside surfactants especially preferred for use herein include those of the Formula A above wherein R is an alkyl group containing from about 9 to about 13 carbon atoms; y is zero; Z is derived from glucose; and x has an average value of from 1 to about 3.

Glycoside surfactants of particular interest for use in the practice of the present invention preferably have a hydrophilic-lipophilic balance (HLB) in the range of from about 10 to about 18 and most preferably in the range of from about 12 to about 14.

The indicated glycoside surfactants are typically employed in the compositions hereof in an amount ranging from about 3 to about 30 weight percent on a total composition weight basis and preferably constitute the predominant surfactant ingredient within said compositions (i.e., preferably representing at least about 50 weight percent of the total surfactant content thereof). Preferably said glycoside surfactants constitute from about 5 to about 20 (most preferably from about 5 to about 15) weight percent of said compositions on a total composition weight basis.

Amphoteric surfactants suitable for use herein can be broadly characterized as being derivatives of aliphatic amines containing a long hydrocarbon chain (typically of from about 8 to about 18 carbon atoms) and an anionic hydrophilic group such as a carboxy group, a sulfonate group, a sulfate group, etc. Examples of such amphoteric surfactants include lauryl/cocamphocarboxy glycinate sulfate, sodium-3-dodecylamino propane sulfonate, cocoamidopropyl betaine, coco/oleamidopropyl betaine, cocoamphocarboxypropionate, lauryl/- cocoamphocarboxyglycinate, laurylamphopropionate, cocoamidopropyl sultaine, lauryl/coco betaine, and the like. Especially preferred amphoteric surfactant components for use herein are the betaine-based and imidazoline-based amphoteric surfactants.

The indicated amphoteric surfactants are preferably employed as the above-described auxiliary surfactant component herein and are typically employed in the compositions hereof in an amount ranging from about 2 to about 30 (preferably from about 2 to about 20 and most preferably from about 3 to about 10) weight percent on a total composition weight basis.

Anionic surfactant components suitable for use herein include long chain (e.g., $C_8$–$C_{20}$) alpha olefin sulfonates; long chain alkyl sarcosinates; long chain alkyl sufosuccinates, long chain alkyl polyethoxy sulfates; alkyl sulfoamides such as N-methyl-N-long chain alkyl taurates; alkyl sulfoesters; linear alkyl benzene sulfonates; higher alkyl (e.g., $C_8$–$C_{20}$) sulfates; alkali metal/fatty acid soaps; long chain (e.g., $C_{10}$–$C_{22}$) aliphatic carboxylate salts and the like.

When the indicated anionic surfactants are employed as auxiliary surfactant components herein, they will typically be employed in an amount ranging from about 2 to about 30 (preferably from about 2 to about 20 and most from about 3 to about 10) weight percent on a total composition weight basis.

In those instances where the auxiliary surfactant component is employed and is composed of a mixture or combination of anionic and amphoteric surfactants, the total amount of such anionic/amphoteric surfactant mixture employed herein will preferably be from about 2 to about 30 (more preferably from about 2 to about 20 and most preferably from about 3 to about 10) weight percent on a total composition weight basis.

Nonionic foam boosting surfactants (or "foam boosters") suitable for use herein include amide and amine oxide surfactant materials. Suitable nonionic amide surfactant materials include those of the formula:

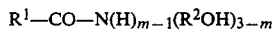

wherein $R^1$ is a saturated or unsaturated aliphatic hydrocarbon radical having from 7 to 21, preferably from 11 to 17 carbon atoms; $R^2$ represents a methylene or ethylene group; and m is 1, 2, or 3, preferably 1 or 2. Specific examples of said amides are mono-ethanol lauryl/coconut fatty acid amide, diethanol dodecyl fatty acid amide, and the like. The monoethanol amides and diethanol amides of $C_{12}$–$C_{14}$ fatty acids are especially preferred amide surfactant species for the purpose of the present invention.

Amine oxide surfactant materials suitable for use herein include semi-polar nonionic compounds of the formula:

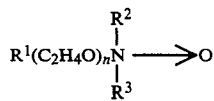

wherein $R^1$ is an alkyl, 2-hydroxyalkyl, 3-hydroxyalkyl, 3-alkoxy-2-hydroxypropyl, or an N-alkyl-3-aminopropyl radical in which the alkyl or alkoxy group contains from about 8 to about 18 carbon atoms, $R^2$ and $R^3$ are methyl, ethyl, propyl, isopropyl, 2-hydroxyethyl, 2-hydroxypropyl, or 3-hydroxypropyl and n is from 0 to about 10. Particularly preferred are amine oxides of the formula:

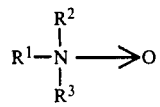

or the formula:

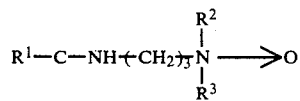

wherein $R^1$ is a $C_{10-14}$ alkyl and $R^2$ and $R^3$ are methyl or ethyl groups. Specific examples of such amine oxide surfactants include cocoamine oxide, laurylamine oxide, lauryl/cocamidopropylamine oxide, etc.

The aforementioned foam booster materials are typically employed in the compositions hereof in an amount ranging from about 1 to about 20 (preferably from about 1 to about 10) weight percent on a total composition weight basis and generally the amount thereof is limited to a level equal to or less than 50 weight percent of the total surfactant content of the subject compositions. Preferably said foam booster material is employed in an amount equal to or less than 33 (more preferably equal to or less than 25 and most preferably equal to or less than 20) weight percent of the combined total surfactant ingredient content within said compositions. Most preferably, the amount of the foam booster material employed in the compositions hereof will range from about 2 to about 5 weight percent based upon the total weight of said compositions.

In a somewhat less preferred embodiment, it is contemplated that anionic surfactant materials such as those described above can be suitably employed in place of all or a portion of the above described nonionic foam booster ingredient. However, the indicated nonionic foam boosting surfactants are generally considered to be milder than normal anionic surfactants and are therefore preferred for use in the present invention.

Water will typically constitute up to about 95 (preferably up to about 90) weight percent of the subject liquid hand-soap or bubble-bath formulations. Most preferably, the water content of said formulations will be from about 70 to about 95 (especially from about 70 to about 90) weight percent on a total composition weight basis.

The total solids or "non-volatiles" content of the present compositions is generally from about 5 to about 30 (preferably from about 10 to about 30 and more preferably from about 10 to about 20) weight percent on a total composition weight basis.

As has been noted above, the viscosity of the liquid detergent compositions of interest herein is at least about 1,000 centipoise. Preferred compositions will have viscosity of from about 1,000 to about 10,000 centipoise and more preferably the viscosity of said compositions will be from about 1,000 to about 5,000 centipoise. Especially preferred compositions will have a minimum viscosity of at least about 1,500 (more preferably at least about 2,000) cps and a maximum viscosity of less than 10,000 (preferably less than 5,000) cps.

In some cases, the viscosity of the above-described compositions will fall within the desired range as prepared using only the above-specified ingredients and without the use viscosity increasing agents or additives. In other cases, however, it may be desirable or necessary to include a viscosifying agent in order to impart the desired viscosity to the subject compositions. Preferred viscosifying agents for use herein include alkali metal or ammonium salts such as sodium chloride, sodium iodide, sodium sulfate, ammonium chloride, ammonium bromide, and, of these, the alkali metal halide and ammonium halide salts (especially ammonium chloride) are particularly preferred. Other viscosifying agents suitable for use herein include water soluble or water dispersible polymeric thickening agents such as carboxymethyl cellulose, hydroxyethyl cellulose, hydroxypropyl cellulose, ethoxylated cellulose, polyacrylic acid polymers, xanthan gum, and the like.

Optional additives or ingredients suitable for use herein generally include those which are normally or conventionally employed in liquid hand-soap and bubble bath formulations such as, for example, moisturizing agents, perfumes, stabilizers, preservatives, sanitizers or disinfectants such as quaternary ammonium halide compounds, colorants (e.g., dyes or pigments), pearlescing agents, and the like. Notably, however, a distinct advantage of certain especially preferred compositions hereof (e.g., those described above which are substantially free of anionic surfactant ingredients) resides in the fact that the inclusion of moisturizing agents, as is required in presently available commercial liquid hand-soap and bubble bath products, is not necessary (and, indeed, is sometimes not desirable) in such especially preferred liquid hand-soap or bubble bath compositions. Thus, certain preferred compositions hereof will also be substantially free of moisturizing ingredients or additives.

Moisturizing agents suitable for use herein (i.e., in those embodiments of the present invention wherein it is desired to employ a moisturizing ingredient or additive) include lanolin, glycerine, ethoxylated lanolin, polyethylene glycols and higher alkyl esters thereof, stearyl alcohol and ethoxylated derivatives thereof, sorbitol, alpha methylglucoside fatty esters (e.g., alpha methylglucoside sesquistearate or dioleate) and ethoxylated derivatives thereof, cationic polymers and copolymers such as acrylamide/dimethyl diallylammonium chloride and the like.

The liquid hand-soap or bubble bath compositions of the present invention can be conveniently prepared in accordance with the known formulation procedures or techniques which are usually employed in the preparation of conventional anionic surfactant-based liquid hand-soap and bubble bath products. Preferably, the desired surfactant components (i.e., the glycoside surfactant, foam booster components, and, if employed, the anionic and/or amphoteric surfactant components) are first dissolved in water and any auxiliary additives which may be desired for use herein such as, for example, stabilizers, perfumes, preservatives, colorants, etc. are subsequently added to the resulting aqueous surfactant solution. Preferably, any such auxiliary ingredients either will be water soluble in character or will be pre-solubilized or pre-dispersed in a portion of the surfactant system prior to being added to the mixture. The application of heat to the aqueous mixture is oftentimes beneficial during the formulation process in facilitating obtention of a homogeneous mixture and it is generally preferred to stir, or to otherwise provide good agitation to the mixture during said process. Further, in those formulations employing a viscosifying agent such as ammonium or alkali metal salts, it is generally preferred to dissolve the desired amount of same in the water at the beginning of the formulation process.

The pH of the present formulations is not particularly critical and can be varied or adjusted as desired in a given instance. As a general rule, however, the pH of such formulations will typically be within the range of from about 6 to about 8.

The present invention is further illustrated and understood by reference to the following examples thereof in which all parts and percentages are on a weight basis unless otherwise indicated.

EXAMPLES 1–14

Liquid hand-soap formulations set forth in Table A below are prepared by dissolving the stated amounts of the indicated glycoside surfactant, amphoteric surfactant and foam booster ingredients in water and by thereafter incorporating, where used, any further moisturizing agents, viscosifying agents, etc. The resulting formulations are then tested or evaluated as to their pH, viscosity, and foaming characteristics. The results of such testing are also summarized in Table A below.

TABLE A

| | Example No. | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| INGREDIENT (weight percent) | | | | | | | | | | | | | | |
| $C_{9-11}$ APG* having an average DP of 1.3 | 13 | 13 | 13 | 13 | 13 | 6.5 | 6.5 | | | 13 | 6.5 | | | |
| $C_{12-13}$ APG* having an average DP of 2.8 | | | | | | | 6.8 | 11.7 | 11.7 | | 5.9 | 11.7 | 11.7 | 13 |
| $C_{12-13}$ APG* having an average DP of 1.3 | | | | | | 6.5 | | | | | | | | |
| Coco/oleamidopropyl betaine | 4.5 | | 4.5 | | 4.5 | 4.5 | 4.5 | 4.5 | 4.5 | | | | | |
| Cocoamidopropyl betaine | | 4.5 | | 4.5 | | | | | | 4.5 | 4.5 | 4.5 | 4.5 | 4.5 |
| Cocoamine oxide | 3.0 | 3.0 | | | | 3.0 | 3.0 | 3.0 | 3.0 | 3.0 | 3.0 | 3.0 | 3.0 | |
| Lauric/myristic diethanol amide | | | 3.5 | 3.0 | | | | | | | | | | 3.0 |
| Coco monoethanol amide | | | | | 3.0 | | | | | | | | | |
| Sodium lauryl sulfate + glycerol stearate (Pearlescence agent) | | | | | | | | 0.8 | 0.8 | 0.8 | 0.8 | | | |
| Acrylamide/dimethyl diallylammonium chloride copolymer (Moisturizing agent) | | | | | | | | | 0.04 | 0.08 | 0.08 | 0.08 | | |
| Water | 79.5 | 79.5 | 79.0 | 79.5 | 79.5 | 79.5 | 79.2 | 80.8 | 79.96 | 78.62 | 79.22 | 79.92 | 80.8 | |
| FORMULATION PROPERTIES | | | | | | | | | | | | | | |
| pH | 6.7 | 6.6 | 6.5 | 6.5 | 6.8 | 6.6 | 6.6 | 6.7 | 7.4 | 6.5 | 6.7 | 6.8 | 6.5 | 8.4 |
| Viscosity (cps) | 660 | 510 | 770 | 480 | 720 | 1120 | 1970 | 5700 | 7000 | 840 | 1330 | 4000 | 1850 | 5300 |
| % $NH_4Cl$ | 6 | 6 | 6 | 6 | 6 | 5 | 4 | | | | | 2 | | |
| Viscosity with $NH_4Cl$ (cps) | 1600 | 1270 | 1380 | 850 | 1110 | 1720 | 2800 | | | | | 2550 | | |
| Foaming Character (0.4%, 25°C.) | | | | | | | | | | | | | | |

TABLE A-continued

| | Example No. | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Ross Miles Foam Test. | | | | | | | | | | | | | | |
| Initial | 140 | 160 | 50 | 40 | 115 | 30 | 140 | 140 | | 80 | | 140 | 150 | 135 |
| 5 Minutes | 130 | 150 | 45 | 40 | 110 | 30 | 130 | 130 | | 75 | | 130 | 145 | 125 |

*Alkyl polyglucoside.

Of the foregoing formulations, those providing relatively stable foams and exhibiting foam heights in the range of from about 110 to 160 are particularly desirable for the purposes of the present invention.

The formulations of Examples 2 and 8–12 are subjected to consumer test panel personal preference testing with regard to their lathering, lather consistency and skin feel characteristics and in comparison with several established, commercially available brand name products. The formulations of Examples 2 and 12 are found to compare very favorably with such established brand name products during said consumer preference testing.

EXAMPLE 15

The following liquid detergent composition is formulated by dissolving the indicated ingredients in water and adjusting the pH thereof to 5.0.

| Ingredient | Amount (Weight Percent) |
|---|---|
| Sodium alpha olefin sulfonate | 8% |
| Sodium lauryl sarcosinate | 3% |
| Cocoamido monoethanol amine | 3% |
| Octadecyl maltoside (D.P. = 2) | 3% |
| Ammonium chloride | 2% |
| Water | 81% |

The resulting composition has a viscosity of 3,100 cps and imparts a soft feeling to the hands upon washing with same.

While the present invention has been described and illustrated by reference to certain specific embodiments and examples thereof, such is not to be interpreted as in any way limiting the scope of the instantly claimed invention.

What is claimed is:

1. A liquid detergent composition which has a viscosity of at least about 1000 centipose and is suitable for use as a liquid hand-soap or bubble bath formulation; which is free of anionic surfactant ingredients; and which comprises, on a total composition weight basis:
   a. from about 3 to about 30 weight percent of a glycoside surfactant;
   b. from about 2 to about 30 weight percent of an amphoteric surfactant;
   c. from about 1 to about 20 weight percent of a nonionic amine oxide or amide foam boosting surfactant, said foam boosting surfactant constituting 50 weight percent or less of the total surfactant content of said composition; and
   d. up to about 95 weight percent water.

2. The composition of claim 1 wherein the glycoside surfactant corresponds to the formula:

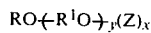   A wherein R is a monovalent organic radical containing from about 6 to about 30 carbon atoms; $R^1$ is a divalent hydrocarbon radical containing from about 2 to about 4 carbon atoms; O is an oxygen atom; y is a number having an average value of from 0 to about 12; Z is a moiety derived from a reducing saccharide containing 5 or 6 carbon atoms; and x is a number having an average value of from 1 to about 10.

3. The composition of claim 2 wherein, in the glycoside surfactant of the Formula A, R is an alkyl group containing from about 9 to about 13 carbon atoms; y is zero; Z is derived from glucose; and x has an average value of from 1 to about 3.

4. The composition of claim 1 wherein the amphoteric surfactant is a betaine surfactant or an imidazoline surfactant.

5. The composition of claim 1 wherein the foam boosting surfactant constitutes 33 weight percent or less of the total surfactant content of said composition.

6. The composition of claim 1 wherein the foam boosting surfactant constitutes 25 weight percent or less of the total surfactant content of said composition.

7. The composition of claim 1 wherein the water content thereof is from about 70 to about 95 weight percent on a total composition weight basis.

8. The composition of claim 1 wherein the viscosity thereof is from about 1,000 to about 10,000 centipoise.

9. The composition of claim 1 wherein the viscosity thereof is from about 1,000 to about 5,000 centipoise.

10. The composition of claim 1 which further comprises an alkali metal or ammonium salt as a viscosifying agent.

11. The composition of claim 10 wherein the viscosifying agent is an alkali metal halide or an ammonium halide.

12. The composition of claim 11 wherein the viscosifying agent is ammonium chloride.

13. The composition of claim 1 wherein same is substantially free of detergency builders, optical brighteners and anti-redeposition ingredients.

14. The composition of claim 1 wherein same is substantially free of moisturizing ingredients.

15. The composition of claim 1 wherein the total solids content thereof is from about 10 to about 30 weight percent on a total composition weight basis.

16. The composition of claim 1 wherein:
   a. the glycoside surfactant constitutes from about 5 to about 15 weight percent of said composition and corresponds to the formula:

   B wherein R is an alkyl group containing from about 9 to about 13 carbon atoms, O is an oxygen atom, Z is a moiety derived from glucose, and x is a number having an average value of from 1 to about 3;
   b. the amphoteric surfactant constitutes from about 3 to about 10 weight percent of said composition and is a betaine or imidazoline surfactant; and
   c. the foam boosting surfactant constitutes from about 2 to about 5 weight percent of said composition and constitutes 25 weight percent or less of the total surfactant content of said composition.

17. The composition of claim 16 wherein the amphoteric surfactant is cocoamidopropyl betaine.

18. The composition of claim 17 wherein the foam boosting surfactant is cocoamine oxide.

19. The composition of claim 1 wherein the viscosity of said composition is at least about 1,500 centipose.

20. The composition of claim 1 wherein the viscosity of said composition is at least about 2000 centipose.

* * * * *